United States Patent [19]
Williams

[11] Patent Number: 6,127,587
[45] Date of Patent: Oct. 3, 2000

[54] FLUORINATION PROCESS

[75] Inventor: Alfred Glyn Williams, Binfield, United Kingdom

[73] Assignee: Zeneca Limited

[21] Appl. No.: 09/403,687

[22] PCT Filed: Mar. 11, 1997

[86] PCT No.: PCT/GB97/00653

§ 371 Date: Sep. 10, 1999

§ 102(e) Date: Sep. 10, 1999

[87] PCT Pub. No.: WO98/40334

PCT Pub. Date: Sep. 17, 1998

[51] Int. Cl.[7] .......................... C07C 17/08; C07C 19/08
[52] U.S. Cl. ..................... 570/168; 570/134; 570/167; 570/169
[58] Field of Search .................. 570/134, 167, 570/168, 169

[56] References Cited

U.S. PATENT DOCUMENTS

| | | |
|---|---|---|
| 2,398,181 | 4/1946 | Johnson . |
| 2,551,573 | 5/1951 | Downing et al. . |
| 2,554,857 | 5/1951 | Gochenour . |
| 4,980,324 | 12/1990 | Kellner at al. . |
| 5,032,648 | 7/1991 | Nicholas . |
| 5,146,015 | 9/1992 | Ll . |
| 5,316,690 | 5/1994 | Ll . |
| 5,739,406 | 4/1998 | Pennetreau et al. ..................... 570/167 |
| 5,760,282 | 6/1998 | Baker et al. ............................ 570/134 |
| 5,852,222 | 12/1998 | Williams et al. . |

FOREIGN PATENT DOCUMENTS

| | | |
|---|---|---|
| 0 581 961 | 2/1994 | European Pat. Off. . |
| 0 699 649 | 3/1996 | European Pat. Off. . |
| 11 56 771 | 11/1963 | Germany . |

*Primary Examiner*—Alan Siegel
*Attorney, Agent, or Firm*—David P. LeCroy

[57] ABSTRACT

The present invention provides a process for the preparation of 1,1-difluoro-1,4-dichlorobutane by reacting 1,1,1,4-tetrachlorobutane or 1,1,4-trichlorobut-1-ene with hydrogen fluoride in the vapor phase.

7 Claims, No Drawings

FLUORINATION PROCESS

The present invention relates to a chlorofluorohydrocarbon and to a novel process for its preparation. More particularly it relates to 1,1-difluoro-1,4-dichlorobutane and a process for preparing it from the known compounds 1,1,1,4-tetrachlorobutane or 1,1,4-trichlorobut-1-ene.

Accordingly the present invention provides a process for preparing 1,1-difluoro-1,4-dichlorobutane comprising reacting 1,1,1,4-tetrachlorobutane or 1,1,4-trichlorobut-1-ene with hydrogen fluoride in the vapour phase.

The process of the present invention when 1,1,1,4-tetrachlorobutane is used is illustrated by the following reaction scheme:

The reaction is conveniently conducted by passing a stream comprising a mixture of the reactants through a heated reaction zone, preferably defined by a tubular vessel whose lining is resistant to corrosion by chemical reaction with hydrogen fluoride, such as for example, one made from "Hastalloy" (Registered Trade Mark) or Monel metal.

The reaction can conveniently be carried out in the presence of a catalyst such as a polyvalent metal halide. Examples of polyvalent metal halides include halides of aluminium, iron, chromium, vanadium, tungsten, tantalum, antimony, titanium, tin, zirconium, nickel, niobium, molybdenum and mercury. Examples of specific catalysts include ferric chloride, particularly in the presence of activated charcoal, aluminium fluoride, aluminium oxide ($\gamma$-alumina), chromium halides such as chromium chloride and chromium fluoride, manganese difluoride, ferric fluoride, cobalt dichloride, nickel difluoride, zirconium fluoride, thorium fluoride, oxyfluorides and antimony pentachloride, particularly in the presence of activated charcoal.

Chromium halides are preferred catalysts and a particularly useful catalyst is chromium (III) chloride. The catalyst may be supported on alumina, preferably one which has been pretreated by treatment with a fluorinating agent such as sulfur tetrafluoride, so as to convert it, at least in part, to aluminium trifluoride.

The reaction temperature is preferably within the range 100 to 400° C., and more preferably within the range 135 to 250° C. The reaction may be conducted under atmospheric pressure or at a pressure above atmospheric pressure, provided that the combination of pressure and temperature is chosen so as to ensure that the reactants and products remain in the vapour phase. The conversion rate is also dependent on various factors such as the residence time in the reaction zone, the ratios of the reactants and the concentration of the reactants as well as the presence of other components of the vapour stream. Preferably the stream contains an inert gaseous diluent to moderate the reaction. Nitrogen is a suitable diluent for this purpose. The reactants and other components of the vapour stream should be free of any water.

The reaction is preferably carried out by passing a gaseous mixture of hydrogen fluoride (which is a volatile material having a boiling point under normal atmospheric pressure of 19.5° C.) together with 1,1,1,4-tetrachlorobutane (or 1,1,4-trichlorobut-1-ene) at an elevated temperature diluted with nitrogen through a reaction zone defined by a metal tube heated to a temperature within the range 130 to 250° C., and thereafter cooling the reactant stream so as to condense out the mixture of reactants and products, which can then be separated by fractional distillation. In a preferred variant of this process a receiving vessel can be used which is equipped with means to permit the hydrogen chloride produced during the reaction to be vented, preferably continuously. This may be achieved by the use of a condenser which liquifies the hydrogen fluoride and the other less volatile components whilst permitting the escape of the more volatile hydrogen chloride gas.

The product mixture consists of the desired 1,1-difluoro-1,4-dichlorobutane, together with unreacted starting material and intermediate species formed during the process. Isolation of the desired product can be achieved readily by fractional distillation and the unreacted starting material and intermediate species recycled back into the reactant stream. One such intermediate species formed during the process when 1,1,1,4-tetrachlorobutane is used as starting material is 1,1,4-trichlorobut-1-ene.

1,1-Difluoro-1,4-dichlorobutane is a novel compound which has useful properties as a solvent, and may be used, for example, in degreasing electrical and electronic components such as printed circuits and the like. Because of its higher boiling point and lower volatility compared with the halomethanes and haloethanes traditionally used for degreasing, and the fact that it is a chlorofluorohydrocarbon and not a chlorofluorocarbon, its use may have environmental advantages. It is also of use as a synthetic chemical intermediate particularly for introducing fluorocarbon functionality into a molecule, for example as a means of introducing the difluorobutenyl group into the nematicidal pyrimidine compounds of International Patent Application no. PCT/GB 93/01912.

Various further preferred features and embodiments of the present invention will now be described with reference to the following non-limiting examples. It will be understood that whereas the Examples disclose experimental procedures which show that the process of the invention can be used to produce the desired product, they may not necessarily disclose the most advantageous conditions for ensuring the economically optimal production of the desired product. Such conditions would be established by a process of routine examination of variation of the conditions within the alternatives and ranges set out herein and any such optimised process may be considered as being included within the scope of the invention.

EXAMPLE 1

This example illustrates the preparation of a chromium (III) chloride catalyst supported on alumminum fluoride.

Alumina pellets (150 g) were packed into a Hastalloy hot tube reactor (length 420 mm, internal diameter 25 mm) and dried by heating for 30 min to 240° C. whilst nitrogen gas was passed through the bed at a rate of 1.0 l/min. The reactor tube was then cooled to 26° C. and sulfur tetrafluoride passed into the tube. The internal temperature increased steadily over 17 min to 160° C. then slowly decreased to 70° C. after which the flow of sulfur tetrafluoride was stopped. After restarting the flow of sulfur tetrafluoride the temperature was observed to increase slowly to 75° then over 6 min further increased very rapidly to 265° C. after which the flow was stopped and the tube cooled to 75° C. The flow of sulfur tetrafluoride was recommenced and a slow exotherm to 90° C. over 10 min observed after which the tube was cooled to 57° C. and the nitrogen purge continued for 1.0 hour. The flow of sulfur tetafluoride was restarted and continued for a further 15 minutes and then stopped. The total amount of sulfur tetrafluoride used was 380 g.

Chromium III chloride (45 g) was suspended in methanol (450 ml) and warmed to 35° C. Zinc powder (1.0 g) was added and the mixture stirred for 35 min, a further 0.35 g of zinc added, heated to 40° C. for a further 10 min and then at 50° C. followed by addition of a further 1.0 g of Zn, followed by one drop of concentrated hydrochloric acid. The temperature of the mixture was observed to increase from 45 to 65° C. (controlled with an ice bath) as the chromium(III) chloride dissolved giving a green slightly cloudy solution. The solution was cooled to ambient and filtered through HiFlo to remove a trace of suspended solids. The volume of the solution was reduced by half by rotary evaporation and the resultant concentrated solution was added to the fluoridated pellets prepared as above after they had been dried by heating to 80° C. and cooled to the ambient temperature under a nitrogen atmosphere. The slurry of pellets was agitated periodically and the remaining solvent removed by evaporation under under reduced pressure. A further 50 ml of methanol was added, the pellets slurried and the excess solvent removed on the rotary evaporator. The pellets were heated to 80° C. under vacuum then allowed to cool under nitrogen. Acetonitrile (50 ml) was added to the pellets and the slurry and after 16 hours the pellets were filtered to remove excess liquid and dried by heating to 80° C. under vacuum for 2 hours. At this stage the pellets were grey green in colour.

The pellets were charged to the Hastalloy hot tube reactor, a chloros scrubber was fitted to the reactor exit and the pellets heated to 370° C. for 4.5 hours under a stream of nitrogen, then cooled to ambient. After 24 hours the packed tube was reheated to 370° C. for 5.75 hours, and stood for 17 hours at ambient temperature. The reactor tube was then heated to 150° C. and gaseous hydrogen fluoride passed through at a rate of 200 ml/min with nitrogen. A steady exotherm occurred with the temperature increasing to a maximum of 192° C. After 15 min the temperature began to decrease and at 175° C. the flow of hydrogen fluoride was stopped and the catalyst pellets allowed to cool under a nitrogen atmosphere.

The hot tube reactor containing the catalyst was then used in the process of the invention as described in the following example.

EXAMPLE 2

This Example illustrates the preparation of 1,1-difluoro-1,4-dichlorobutane by the process of the invention.

The Hastalloy hot tube reactor containing the chromium (III) chloride catalyst prepared as described in the previous Example was fitted at one end with inlet ports to allow controlled ingress of gaseous hydrogen fluoride, and 1,1,1,4-tetrachlorobutane and a flow of nitrogen, and was connected at the other end to a cold trap maintained at −78° C. The tube was heated to 160° C. and the nitrogen flow rate set at 200 ml/min. Hydrogen fluoride (19.4 g) was fed at a rate of 300 ml/min and 1,1,1,4-tetrachlorobutane (2.0 ml) fed at a rate of 0.1 ml/min. The hydrogen fluoride addition was continued for 3 minutes after the tetrachlorobutane addition was complete. The contents of the cold trap were collected by washing out with dichloromethane (5×10 ml) the washings combined and treated with iced water to remove hydrogen fluoride and the organic phase washed with water and dried over anhydrous magnesium sulfate. The solvent was removed by careful distillation using a knitmesh column (length 77 mm, diameter 8 mm) and the residual liquid analysed by gas-liquid chromatography/mass spectrometry, revealing that the product mixture contained 1,1-difluoro 1,4-dichlorobutane (identity confirmed by proton NMR and Mass Spectroscopy) unreacted 1,1,1,4-tetrachlorobutane and 1,1,4-trichlorobutene in the ratio 7:32:2.

Data for 1,1,-difluoro-1,4-dichlorobutane:

$^1$H nmr (CDCl$_3$): 2.15 (m, 2H, CH$_2$); 2.50 (m, 2H, CH$_2$CF$_2$Cl); 3.55 (br t, 2H, CH$_2$Cl). MS: 142 (M+−HF), 127 (M+−Cl).

What is claimed is:

1. A process for preparing 1,1-difluoro-1,4-dichlorobutane comprising reacting 1,1,1,4-tetrachlorobutane or 1,1,4-trichlorobut-1-ene with hydrogen fluoride in the vapour phase.

2. A process according to claim 1 carried out in the presence of a catalyst selected from polyvalent metal halides and aluminium oxides.

3. A process according to claim 2 wherein the polyvalent metal halide is selected from halides of aluminium iron, chromium, vanadium, tungsten, antimony, tantalum, titanium, zirconium, tin, nickel, niobium, molybdenum, and mercury.

4. A process according to claim 2 wherein the polyvalent metal halide is selected from ferric chloride, aluminium fluoride, chromium chloride, chromium fluoride, manganese difluoride, ferric fluoride, cobalt dichloride, nickel difluoride, zirconium fluoride, thorium fluoride, oxyfluorides and antimony pentachloride, optionally in the presence of activated charcoal.

5. A process according to claim 3 wherein the polyvalent metal halide is selected from chromium halides.

6. A process according to claim 5 wherein the chromium halide is chromium (III) chloride.

7. A process according to claim 2 carried out at a temperature within the range 130 to 400° C.

* * * * *